US012760165B2

(12) United States Patent
Connor et al.

(10) Patent No.: US 12,760,165 B2
(45) Date of Patent: Oct. 13, 2026

(54) UPCYCLING OF PLASTIC WASTE TO RECOMBINANT SILK PROTEINS VIA PSEUDOMONAS BACTERIA

(71) Applicant: Rensselaer Polytechnic Institute, Troy, NY (US)

(72) Inventors: Alexander Joseph Connor, Slingerlands, NY (US); Runye Helen Zha, Troy, NY (US); Mattheos Ag Koffas, Niskayuna, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 403 days.

(21) Appl. No.: 18/546,449

(22) PCT Filed: Feb. 16, 2022

(86) PCT No.: PCT/US2022/016546

§ 371 (c)(1),
(2) Date: Aug. 15, 2023

(87) PCT Pub. No.: WO2022/177949

PCT Pub. Date: Aug. 25, 2022

(65) Prior Publication Data

US 2025/0019512 A1 Jan. 16, 2025

Related U.S. Application Data

(60) Provisional application No. 63/310,635, filed on Feb. 16, 2022, provisional application No. 63/149,790, filed on Feb. 16, 2021.

(51) Int. Cl.

| | |
|---|---|
| ***C08J 11/10*** | (2006.01) |
| ***C07K 14/435*** | (2006.01) |
| ***C07K 14/78*** | (2006.01) |
| ***C12N 1/205*** | (2026.01) |
| ***C12N 15/78*** | (2006.01) |
| ***C12R 1/385*** | (2006.01) |
| ***C12R 1/40*** | (2006.01) |

(52) U.S. Cl.

CPC ....... *C08J 11/105* (2013.01); *C07K 14/43504* (2013.01); *C07K 14/78* (2013.01); *C12N 1/205* (2021.05); *C12N 15/78* (2013.01); *C12N 2510/02* (2013.01); *C12R 2001/385* (2021.05); *C12R 2001/40* (2021.05)

(58) Field of Classification Search

CPC ........ C08J 11/105; C12N 1/205; C12N 15/78; C12N 2510/02; C07K 14/43504; C07K 14/78; C12R 2001/385; C12R 2001/40

See application file for complete search history.

(56) References Cited

U.S. PATENT DOCUMENTS

| | | | | |
|---|---|---|---|---|
| 7,960,154 | B1 | 6/2011 | Nakajima et al. | |
| 8,034,897 | B1 | 10/2011 | Scheibel | |
| 8,481,681 | B2 | 7/2013 | Sutherland | |
| 9,051,383 | B2 | 6/2015 | Hayashi | |
| 10,124,512 | B2 | 11/2018 | Boisart et al. | |
| 10,435,516 | B2 | 10/2019 | Widmaier | |
| 10,647,975 | B2 | 5/2020 | Gamboa | |
| 11,192,982 | B2 | 12/2021 | Widmaier | |
| 2015/0247018 | A1 | 9/2015 | Yang et al. | |
| 2019/0116768 | A1 | 4/2019 | Brigham | |
| 2019/0375639 | A1 | 12/2019 | Orbaek White et al. | |
| 2020/0291078 | A1 * | 9/2020 | Joshi | C07K 14/78 |
| 2021/0094989 | A1 | 4/2021 | Sutherland | |

FOREIGN PATENT DOCUMENTS

| | | | |
|---|---|---|---|
| CN | 102181378 | B | 10/2012 |
| CN | 107794252 | B | 7/2021 |
| JP | 2018064542 | A | 4/2018 |
| WO | 2003057720 | A2 | 7/2003 |
| WO | 2004038016 | A1 | 5/2004 |
| WO | 2005068495 | A1 | 7/2005 |
| WO | 2006041225 | A1 | 4/2006 |
| WO | 2007025719 | A1 | 3/2007 |
| WO | 2015067619 | A2 | 5/2015 |
| WO | 2017087827 | A1 | 5/2017 |
| WO | 2019222396 | A1 | 11/2019 |

OTHER PUBLICATIONS

Aparicio T, de Lorenzo V, Martínez-García E. CRISPR/Cas9-Based Counterselection Boosts Recombineering Efficiency in Pseudomonas putida. Biotechnol J. May 2018;13(5):e1700161. doi: 10.1002/biot.201700161. Epub Dec. 4, 2017. PMID: 29058367. (Year: 2017).*

Choi KH, Schweizer HP. mini-Tn7 insertion in bacteria with single attTn7 sites: example Pseudomonas aeruginosa. Nat Protoc. 2006;1(1): 153-61. doi: 10.1038/nprot.2006.24. PMID: 17406227. (Year: 2006).*

International Search Report and The Written Opinion of the International Searching Authority, International Application No. PCT/US2022/016546, mailed Jul. 8, 2022.

(Continued)

*Primary Examiner* — Louise W Humphrey
*Assistant Examiner* — Rachel Emily Martin
(74) *Attorney, Agent, or Firm* — Barclay Damon LLP; Anthony P. Gangemi

(57) ABSTRACT

Customized recombinant proteins are designed and produced by cultures of *Pseudomonas* bacteria, including natural and recombinant silk proteins, fluorescent proteins, and elastin-like proteins (ELPs). The recombinant genes can be expressed via insertion directly into the *Pseudomonas* bacteria, or via the transformation of a suitably designed recombinant plasmid. Advantageously, the carbon source used as the nutrient source by the *Pseudomonas* bacteria is derived from non-traditional nutrient sources, such as exogenous rhamnolipids, hydrocarbons, polyolefins, polyesters, and pyrolysis products of waste plastic, e.g., pyrolysis products of polyethylene or poly(ethylene terephthalate). The waste feedstocks can be added to particularly designed growth media for sustained bacterial culture and protein production. These feedstocks allow for upcycling of plastic waste into high value protein products, such as recombinant silk fibroins.

4 Claims, 11 Drawing Sheets

Specification includes a Sequence Listing.

(56) References Cited

OTHER PUBLICATIONS

Aparicio, T., et al., "High-Efficiency Multi-site Genomic Editing of Pseudomonas putida through Thermoinducible ssDNA Recombineering," iScience, vol. 23, pp. 1-10, Mar. 27, 2020.
Guzik, M.W., et al., "Conversion of post consumer polyethylene to the biodegradable polymer polyhydroxyalkanoate," Applied Microbiology and Biotechnology, vol. 98, No. 9, Jan. 12, 2014.
Utomo, R.N.C., et al., "Defined Microbial Mixed Culture for Utilization of Polyurethane Monomers," ACS Sustainable Chemistry & Engineering, vol. 8, pp. 17466-17474, Nov. 2020.

* cited by examiner

SEQUENCE LISTING

```
<160> NUMBER OF SEQ ID NOS: 4

<210> SEQ ID NO 1
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 1

Gly Pro Gly Gln Gln Ala Ala Ala Ala Ala Gly Pro Gly Gln Gln Gly
1               5                   10                  15

Pro Gly Gln Gln Gly Pro Gly Gln Gln Gly Pro Gly Glu Gln Gly Pro
            20                  25                  30

Gly Ser Gly
        35


<210> SEQ ID NO 2
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 2

Gly Pro Gly Gln Gln Ala Ala Ala Ala Ala Ala Ala Ala Ala Ala Gly
1               5                   10                  15

Pro Gly Gln Gln Gly Pro Gly Gln Gln Gly Pro Gly Glu Gln Gly Pro
            20                  25                  30

Gly Ser Gly
        35
```

-continued

```
<210> SEQ ID NO 3
<211> LENGTH: 50
<212> TYPE: PRT
<213> ORGANISM: Artificial Sequence
<220> FEATURE:
<223> OTHER INFORMATION: Synthetic Polypeptide

<400> SEQUENCE: 3

Val Pro Gly Ala Gly Val Pro Gly Ala Gly Val Pro Gly Ala Gly Val
1               5                   10                  15

Pro Gly Ala Gly Val Pro Gly Tyr Gly Val Pro Gly Ala Gly Val Pro
            20                  25                  30

Gly Ala Gly Val Pro Gly Ala Gly Val Pro Gly Ala Gly Val Pro Gly
        35                  40                  45

Tyr Gly
    50


<210> SEQ ID NO 4
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 4

Val Pro Gly Ala Gly Val Pro Gly Ala Gly Val Pro Gly Ala Gly Val
1               5                   10                  15

Pro Gly Ala Gly Val Pro Gly Tyr Gly Val Pro Gly Ala Gly Val Pro
            20                  25                  30

Gly Ala Gly Val Pro Gly Ala Gly Val Pro Gly Ala Gly Val Pro Gly
        35                  40                  45

Tyr Gly Val Pro Gly Ala Gly Val Pro Gly Ala Gly Val Pro Gly Ala
    50                  55                  60

Gly Val Pro Gly Ala Gly Val Pro Gly Tyr Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Tyr Gly Gly Arg Gly Asp Ser
            100                 105
```

UPCYCLING OF PLASTIC WASTE TO RECOMBINANT SILK PROTEINS VIA PSEUDOMONAS BACTERIA

CROSS REFERENCE TO RELATED APPLICATION(S)

This application is a national stage filing of International Patent Application No. PCT/US2022/016546, filed Feb. 16, 2022, which claims the benefit of U.S. Provisional Application Nos. 63/149,790, filed Feb. 16, 2021, and 63/310,635, filed Feb. 16, 2022, which are incorporated by reference as if disclosed herein in their entireties.

STATEMENT REGARDING FEDERALLY SPONSORED RESEARCH AND DEVELOPMENT

The contents of the file named "Sequences.txt", which was created on Feb. 15, 2024 and is 2.6 KB in size, are hereby incorporated by reference in their entireties.

BACKGROUND

The overwhelming majority of plastics used today are derived from petrochemical feedstocks and are considered "recalcitrant", meaning they are not readily degraded in most natural environments. Even with ideal application of conventional recycling strategies, these plastics can only be recycled a limited number of times before end-of-life disposal by incineration or dumping in landfills, leading ultimately to greenhouse gas emissions, pollution and disruption of natural ecosystems, and loss of feedstock material. Polyethylene and poly(ethylene terephthalate) are especially problematic, as they are predominantly used for short lifespan applications such as single-use packaging. Furthermore, chemical recycling or depolymerization of these polymers are non-trivial and require substantial energy costs.

These challenges have led to a growing interest in processes that convert waste materials into higher value products that may share little to no chemical similarity with the starting material. This process, known as "upcycling", has been widely applied to produce value-added fuels, chemicals, and materials, through methods such as pyrolysis and catalytic conversion reactions. Microbial upcycling is another strategy, which unlike the aforementioned approaches, has the ability to readily produce biodegradable and/or biologically active materials. Thus, microbial upcycling is a promising end-of-life option for recalcitrant waste plastic while simultaneously producing high value materials.

Upcycling of plastics using microbial cultures has been used to produce several biodegradable materials, such as polyhydroxyalkanoate (a biodegradable plastic), fatty acids, and biosurfactants. These materials represent only a small fraction of what recombinant microbes are capable of producing. As living organisms, they possess the ability to synthetize myriad biochemicals that include but are not limited to protein or polysaccharide-based biomaterials, secondary metabolites, and enzymes. Some of these materials cannot be readily synthesized without the use of recombinant microbial systems. Thus, the development of microbial platforms that can upcycle recalcitrant hydrocarbon materials to high value products is of high utility.

The body of literature exploring the upcycling capabilities of bacteria has grown considerably in the past five years. For instance, platforms such as *Escherichia coli* and *Bacilis succiniciproducens* have been used to produce high-value metabolites from the upcycling of organic biomass such as starch and lignin waste. Likewise, the upcycling of recalcitrant plastic, such as poly(ethylene terephthalate) into high value compounds has been established in species such as *E. coli.*

Central to the field of microbial plastics upcycling is the *Pseudomonas* genus. Several *Pseudomonas* species, including strains utilized in these methods, demonstrate the ability to naturally use carbon-based plastics as a carbon nutrient source, as well as high growth rates when using these carbon sources compared to other bacteria. However, the high value compounds produced by these microorganisms, including *Pseudomonas*, have almost exclusively targeted endogenous bacterial biopolymers, such as polyhydroxyalkanoate, or secondary metabolites as products. Bacterial upcycling of waste into recombinant proteins would expand the usefulness and value of upcycling technologies. Despite this, bacterial upcycling to proteins with precisely designed sequences is rare, and studies in this space have used readily digestible organic waste as a feedstock, such as cheese whey or waste algae, rather than recalcitrant feedstock. Moreover, none of these studies have targeted the production of recombinant proteins, such as silk fibroin or protein-based fluorophores using *Pseudomonas* bacteria consuming non-traditional carbon sources.

Notwithstanding, *Pseudomonas* bacteria represent an advantageous chassis for recombinant protein production while using non-traditional carbon sources, which can form the basis for a microbial system that upcycles recalcitrant plastic into high value products. It has been documented that *Pseudomonas* species are capable of expressing a myriad of recombinant proteins, often using vector systems that are similar, if not identical to those available for heterologous expression in *E. coli*. Over the past two decades it has been common practice for researchers who study *Pseudomonas* biofilms to visualize their formation through recombinant green fluorescent protein (GFP) expression. The plasmids used for this expression contain state-of-the-art features including inducible expression of GFP, antibiotic selection mechanisms, various copy numbers, and titratable promoter strength. Recombinant *Pseudomonas* hosts, including *Pseudomonas fluorescens* and *aeruginosa*, have also been used to produce a diverse array of heterologous proteins including human granulocyte colony-stimulating factor, antibody derivatives, penicillin G acylase, and insecticidal proteins. In a biomanufacturing setting, *Pseudomonas* species share many characteristics with *E. coli* that have allowed to the latter to become a workhorse of heterologous protein production, including the ability to grow to cell densities above 100 g/L and produce recombinant proteins at levels above 50% total cell protein. Recombinant *Pseudomonas* systems are also capable of performing secretion of product protein, a capability that is highly prized in heterologous protein production.

Conventionally, natural silk is harvested from the cocoons of domesticated *B. mori* silkworm for use in textiles, cosmetic formulations, and biomedical applications. Sold globally at a scale of 160,000 metric tons per year, *B. mori* silk production has intensive land and water requirements due to the amount of mulberry leaves necessary to sustain the silkworms through their fifth instar stage, at which point a cocoon is spun. Thus, the use of current sericulture techniques as a means to manufacture silk for consumer plastics applications is not environmentally sustainable or economical. Furthermore, the properties of silk fibroin derived from silkworms or other organisms in nature, such as spiders (which cannot be farmed due to their cannibalistic nature), are not readily tunable at the primary sequence level.

Developments in biomanufacturing of silk have focused on synthesis of recombinant proteins mimicking the structure of native silk fibroin, facilitated in the last few decades by the elucidation of partial or whole DNA sequences of these proteins from various species. Given the large size (180-720 kDa) and highly repetitive nature of silk fibroin, isolation of silk fibroin genes by polymerase chain reaction for recombinant plasmid construction is typically not feasible. A general approach is de novo synthesis of a gene fragment encoding for one beta-sheet/non-beta-sheet diblock sequence, typically inspired by the amino acid motifs found in various native silk fibroin, with subsequent iterative directional ligation of these tandem repeats to construct the full-length gene. Early work explored *E. coli* and *Pichia pastoris* expression hosts. Since then, researchers have experimented with other hosts for recombinant silk fibroin production, including insect and BmN cells (isolated from *B. mori*), tobacco and potato cells, and even transgenic silkworm, mice, and goats. *E. coli* remains the most widely used microbial host for producing recombinant silk fibroins.

While several hosts have been investigated for recombinant silk production, the field is limited by a lack of exploration into non-traditional bacterial expression platforms. Moreover, investigation and engineering of processes related to upcycling waste materials, whether organic or inorganic, into high-value silk proteins is lacking.

SUMMARY

Aspects of the present disclosure include a method of upcycling plastics. In some embodiments, the method includes inserting one or more exogenous genes into a plurality of *Pseudomonas* sp. bacteria to form recombinant *Pseudomonas* sp. bacteria, preparing a growth medium including the recombinant *Pseudomonas* sp. bacteria, producing a product from the recombinant *Pseudomonas* sp. bacteria via expression of the one or more exogenous genes, and isolating the product from the growth medium.

In some embodiments, the growth medium includes a carbon component including a concentration of exogenous rhamnolipids; hydrocarbyl groups including between about 5 and about 32 carbon atoms; pyrolysis products of a polyolefin; pyrolysis products of a polyester; a polyethylene component including polyethylene terephthalate, pyrolysis products of a polyethylene, or combinations thereof; or combinations thereof. In some embodiments, the *Pseudomonas* sp. bacteria includes *P. aeruginosa* RR1, *P. aeruginosa* NCIMB 14923, *P. oleovorans, P. putida* GPo1, or combinations thereof. In some embodiments, the carbon component provides between about 0.05% and about 2% w/v carbon available to the recombinant *Pseudomonas* sp. bacteria. In some embodiments, the growth medium comprises a salt component including about 9 g/L $Na_2HPO_4 \cdot 12H_2O$, about 1.5 g/L $KH_2PO_4$, about 0.2 g/L $MgSO_4 \cdot 7H_2O$, about 20 mg/L $CaCl_2$, about 1.2 mg/L Fe(III)$NH_4$ citrate, about 4 mg/L $ZnSO_4 \cdot 7H_2O$, about 10 mg/L $FeSO_4 \cdot 7H_2O$, about 1 mg/L $CuCl_2 \cdot 2H_2O$, about 1 mg/L $MnCl_2 \cdot 4H_2O$, about 1 mg/L $Na_2B_4O_7 \cdot 10H_2O$, about 0.2 mg/L $NiCl_2 \cdot 6H_2O$, and about 0.3 mg/L $Na_2MoO_4 \cdot 2H_2O$. In some embodiments, the growth medium further comprises a nitrogen source including ammonium chloride, ammonium nitrate, or combinations thereof. In some embodiments, the ammonium chloride is included in the growth medium at a concentration between about 0.25 g/L and about 5 g/L, the ammonium nitrate is included in the growth medium at a concentration between about 0.19 g/L and about 3.8 g/L, or combinations thereof. In some embodiments, the one or more exogenous genes encode silk proteins, fluorescent proteins, elastin-like proteins, or combinations thereof. In some embodiments, the one or more exogenous genes comprise gene fragments including a construction having between about 2 and about 64 repeated fragments. In some embodiments, the gene fragments code for the peptide GPGQQ AAAAA GPGQQ GPGQQ GPGQQ GPGEQ GPGSG (SEQ ID NO.: 1), GPGQQ AAAAA AAAAA GPGQQ GPGQQ GPGEQ GPGSG (SEQ ID NO.: 2), or combinations thereof.

Aspects of the present disclosure include a method for producing recombinant silk proteins. In some embodiments, the method includes providing a *Pseudomonas* sp. bacterium, inserting one or more genes encoding silk proteins to form a recombinant *Pseudomonas* sp. bacterium, and expressing the one or more genes. In some embodiments, the silk proteins are natural silk proteins, recombinant silk proteins, or combinations thereof. In some embodiments, the one or more genes encoding silk proteins are inserted at an attTn7 site of the recombinant *Pseudomonas* sp. bacterium under the control of a tac promoter and a lac operon.

In some embodiments, inserting one or more genes encoding silk proteins to form a recombinant *Pseudomonas* sp. bacterium includes providing a plasmid compatible with the *Pseudomonas* sp. bacterium, inserting a plurality of gene fragments encoding silk proteins to form a recombinant plasmid, and transforming the recombinant plasmid into the *Pseudomonas* sp. bacteria. In some embodiments, the method includes multiplying at least one of the gene fragments so the recombinant plasmid includes multiple copies of the gene fragment, wherein the at least one gene fragment is multiplied between about 2 and about 64 times.

In some embodiments, the gene fragments code for GPGQQ AAAAA GPGQQ GPGQQ GPGQQ GPGEQ GPGSG (SEQ ID NO.: 1), GPGQQ AAAAA AAAAA GPGQQ GPGQQ GPGEQ GPGSG (SEQ ID NO.: 2), or combinations thereof. In some embodiments, the plasmid includes a pSEVA plasmid backbone. In some embodiments, the *Pseudomonas* sp. bacterium includes *P. aeruginosa* RR1, *P. aeruginosa* NCIMB 14923, *P. oleovorans, P. putida* GPo1, or combinations thereof.

Aspects of the present disclosure include a recombinant bacterium. In some embodiments, the recombinant bacterium includes a *Pseudomonas* sp. bacterium including one or more biosynthetic pathways that utilize as a carbon source: exogenous rhamnolipids; hydrocarbyl groups including between about 5 and about 32 carbon atoms; pyrolysis products of a polyolefin; pyrolysis products of a polyester; a polyethylene component including polyethylene terephthalate, pyrolysis products of a polyethylene, or combinations thereof, or combinations thereof. In some embodiments, the recombinant bacterium includes one or more genes encoding silk proteins. In some embodiments, the one or more genes comprise gene fragments including a construction having between about 2 fragment and about 64 repeated fragments. In some embodiments, the gene fragments code for GPGQQ AAAAA GPGQQ GPGQQ GPGQQ GPGEQ GPGSG (SEQ ID NO.: 1), GPGQQ AAAAA AAAAA GPGQQ GPGQQ GPGEQ GPGSG (SEQ ID NO.: 2), or combinations thereof. In some embodiments, the *Pseudomonas* sp. bacteria includes *P. aeruginosa* RR1, *P. aeruginosa* NCIMB 14923, *P. oleovorans, P. putida* GPo1, or combinations thereof.

In some embodiments, the one or more genes encoding silk proteins are inserted at a attTn7 site of the *Pseudomonas* sp. bacteria under the control of a tac promoter and a lac operon. In some embodiments, the one or more genes encoding silk proteins are included in the bacterium in a recombinant plasmid. In some embodiments, the recombinant plasmid includes a pSEVA plasmid backbone including inducible expression of the one or more genes with isopropyl ß-D-1-thiogalactopyranoside.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DESCRIPTION

Some embodiments of the present disclosure are directed to a method of using recombinant bacteria for the production of one or more desired products using hydrocarbyl materials as a carbon source. In some embodiments, the desired products are a natural protein product, a recombinant protein product, or combinations thereof. In some embodiments, the bacteria is a recombinant *Pseudomonas* sp. bacteria. In some embodiments, the recombinant bacteria is modified to express one or more exogenous genes encoding the desired product, e.g., the protein product. In some embodiments, the one or more exogenous genes are composed of a plurality of gene fragments. In some embodiments, the recombinant bacteria is modified to express one or more exogenous gene fragments encoding the desired product. In some embodiments, the one or more exogenous gene fragments are repeated between about 2 and about 64 times and, when expressed together, produce the desired product. In some embodiments, the one or more exogenous genes are inserted into and expressed from the genome of the recombinant bacteria. In some embodiments, the one or more exogenous genes are inserted into a plasmid compatible with the recombinant bacteria, the recombinant plasmid then being transformed into the recombinant bacteria and expressed in the recombinant bacteria. In some embodiments, the desired products include silk proteins, fluorescent proteins, elastin-like proteins, or combinations thereof.

In some embodiments, the hydrocarbyl material is a natural carbon source, a synthetic carbon source, or combinations thereof. In some embodiments, the hydrocarbyl material is a natural polymeric feedstock, a synthetic polymeric feedstock, or combinations thereof. In some embodiments, the hydrocarbyl material is a petroleum-based plastic or derived from petroleum-based plastics. In some embodiments, the hydrocarbyl material is a post-consumer waste material including one or more plastics or derived from the waste material. Thus, the embodiments of the present disclosure enable the "upcycling" of recalcitrant plastics present, e.g., as a byproduct of an industrial process, into one or more useful products. Exemplary embodiments of these and other embodiments of the present disclosure are described in greater detail below.

Figure 1:
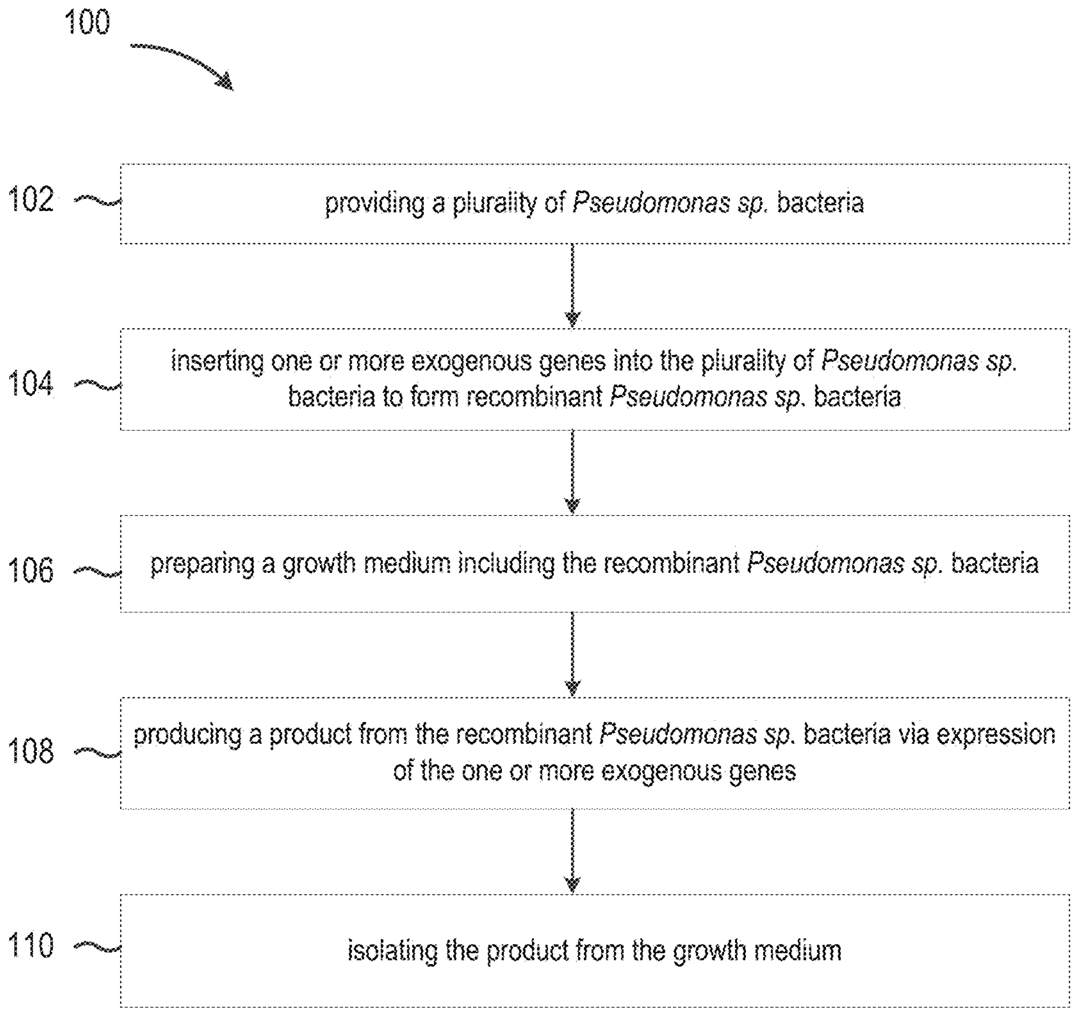
FIG. 1 is a chart of a method of converting a hydrocarbyl material into a desired product using recombinant bacteria according to some embodiments of the present disclosure.

Referring now to FIG. 1, some embodiments of the present disclosure are directed to a method 100 of converting a hydrocarbyl material into a desired product, e.g., a method of upcycling plastics. At 102, a plurality of *Pseudomonas* sp. bacteria are provided. In some embodiments, the *Pseudomonas* sp. bacteria include one or more biosynthetic pathways that utilize the hydrocarbyl material (and/or its components, derivatives, byproducts, etc.) as a carbon source. Briefly, the *Pseudomonas* sp. bacteria express genes encoding one or more proteins having activity, alone or in some combination, to break down the hydrocarbyl material and/or its derivatives into small molecules for use in one or more biosynthetic pathways that sustain the host system, e.g., via the Krebs cycle. In some embodiments, the hydrocarbyl material includes or is derived from posts-consumer waste. In some embodiments, the hydrocarbyl material includes exogenous rhamnolipids; hydrocarbyl groups including between about 5 and about 32 carbon atoms, e.g., hexadecane; pyrolysis products of a polyolefin; pyrolysis products of a polyester; a polyethylene component including polyethylene terephthalate, pyrolysis products of a polyethylene, or combinations thereof; or combinations thereof. In some embodiments, the *Pseudomonas* sp. bacteria includes *P. aeruginosa* RR1*, P. aeruginosa* NCIMB 14923*, P. oleovorans, P. putida* GPo1, or combinations thereof.

At 104, one or more exogenous genes are inserted into the *Pseudomonas* sp. bacteria to form recombinant *Pseudomonas* sp. bacteria. When the one or more exogenous genes are expressed by the recombinant *Pseudomonas* sp. bacteria, the desired product is produced. In some embodiments, the one or more exogenous genes encode silk proteins, fluorescent proteins, elastin-like proteins, or combinations thereof, as will be discussed in greater detail below. While the exemplary embodiments discuss expression of exogenous genes in recombinant *Pseudomonas* sp. bacteria for the production of silk proteins, fluorescent proteins, and elastin-like proteins as desired products, the present disclosure is not intended to be limiting in this regard, as exogenous genes for the production of other desired products can also be included in the recombinant *Pseudomonas* sp. bacteria. In some embodiments, the silk proteins include natural silk proteins, recombinant silk proteins, different permutations of synthetic silk proteins, proteins in which one or more characteristics overlap with those of silk proteins, i.e., primary sequence, primary function, aggregation prone, intrinsic disorder, etc., or combinations thereof. In some embodiments, the fluorescent proteins include green fluorescent protein.

Still referring to FIG. 1, at 106, a growth medium including the recombinant *Pseudomonas* sp. bacteria is prepared. In some embodiments, the growth media includes a concentration of carbon from natural sources, a concentration of carbon from synthetic sources, or combinations thereof. In some embodiments, the growth medium includes a polymer feedstock. In some embodiments, the polymer feedstock is pre-treated, e.g., using pyrolysis to create the carbon source for bacteria growth during recombinant protein production. In some embodiments, growth medium includes a carbon component. In some embodiments, the carbon component includes a concentration of the hydrocarbyl material discussed above, e.g., exogenous rhamnolipids; hydrocarbyl groups including between about 5 and about 32 carbon atoms; pyrolysis products of a polyolefin; pyrolysis products of a polyester; a polyethylene component including polyethylene terephthalate, pyrolysis products of a polyethylene, or combinations thereof; or combinations thereof. In some embodiments, the hydrocarbyl groups can be linear, branched, aromatic, saturated, unsaturated, or combinations thereof. In some embodiments, the hydrocarbyl groups include hydrocarbons of different sizes, saturation levels, structures, etc. The products of polyethylene pyrolysis vary, but can generally be viewed as a distribution of aliphatic hydrocarbons, ranging from C8-C32, of which 90% are alkanes and 10% are alkenes. Without wishing to be bound by theory, the bulk of the distribution is comprised of C9-C27 hydrocarbons.

In some embodiments, one of the exogenous rhamnolipids, hydrocarbyl groups including between about 5 and about 32 carbon atoms, pyrolysis products of a polyolefin, pyrolysis products of a polyester, or polyethylene component is the sole carbon source for the recombinant *Pseudomonas* sp. bacteria in the growth medium. In some embodiments, the carbon component provides between about 0.05% and about 2% w/v carbon available to the recombinant *Pseudomonas* sp. bacteria.

In some embodiments, the growth medium comprises a minimal salt media. In some embodiments, the growth medium includes common laboratory minimal or complex media, e.g., Luria Broth. In some embodiments, the growth medium includes a salt component including about 9 g/L $Na_2HPO_4 \cdot 12H_2O$, about 1.5 g/L $KH_2PO_4$, about 0.2 g/L $MgSO_4 \cdot 7H_2O$, about 20 mg/L $CaCl_2$, about 1.2 mg/L Fe(III) $NH_4$ citrate, about 4 mg/L $ZnSO_4 \cdot 7H_2O$, about 10 mg/L $FeSO_4 \cdot 7H_2O$, about 1 mg/L $CuCl_2 \cdot 2H_2O$, about 1 mg/L $MnCl_2 \cdot 4H_2O$, about 1 mg/L $Na_2B_4O_7 \cdot 10H_2O$, about 0.2 mg/L $NiCl_2 \cdot 6H_2O$, and about 0.3 mg/L $Na_2MoO_4 \cdot 2H_2O$. In some embodiments, the growth medium includes a nitrogen source. In some embodiments, the nitrogen source includes ammonium chloride, ammonium nitrate, or combinations thereof. In some embodiments, ammonium chloride is included in the growth medium at a concentration between about 0.25 g/L and about 5 g/L. In some embodiments, ammonium nitride is included in the growth medium at a concentration between about 0.19 g/L and about 3.8 g/L.

At 108, the product is produced from the recombinant *Pseudomonas* sp. bacteria via expression of the one or more exogenous genes. At 110, the product is then isolated from the growth medium.

Figure 2:
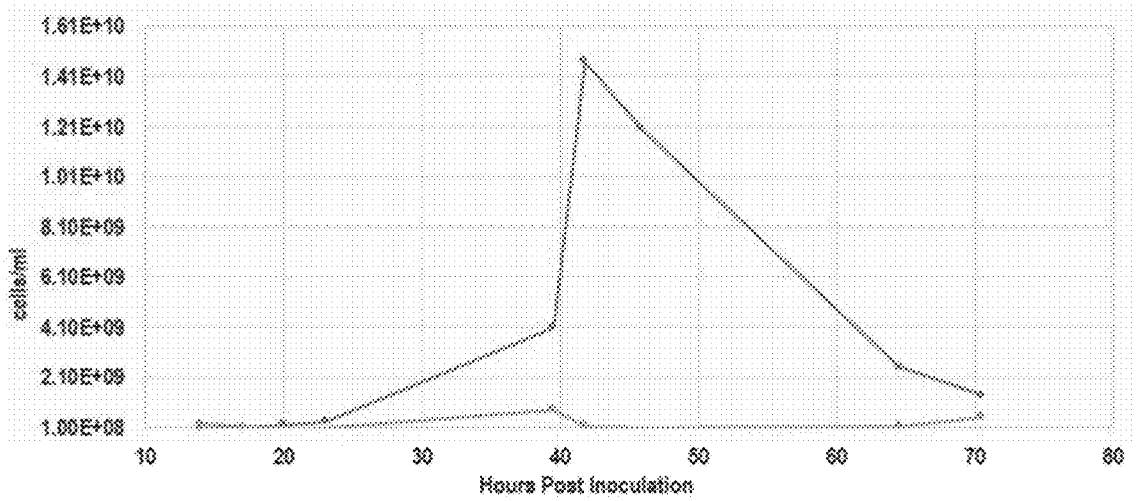
FIG. 2 is a graph showing growth of *P. aeruginosa* with rhamnolipids and hexadecane as carbon source.

Referring now to FIG. 2, an exemplary embodiment is shown that demonstrates growth of *P. aeruginosa* at 37° C. when 0.5 g/L exogenous rhamnolipids and 1% w/v hexadecane are supplied as carbon sources in the cell culture, with either 5 g/L ammonium chloride (blue) or 3.8 g/L ammonium nitrate (orange) supplied as the nitrogen source. At slightly over 40 hours after inoculation, the cells/ml in the culture including ammonium chloride, but not the culture containing ammonium nitrate, reached levels comparable to those achieved when culturing for 18-24 hours in complex media ($1 \times 10^9$-$1 \times 10^{10}$ cells/ml).

Figure 3:
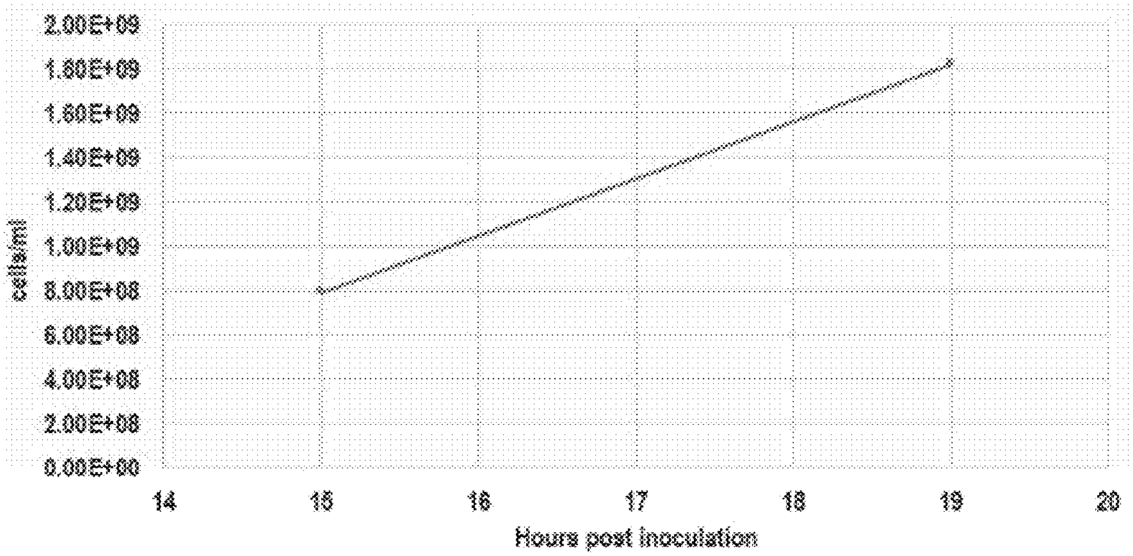
FIG. 3 is a graph showing growth of *P. aeruginosa* with rhamnolipids as the sole carbon source.

Referring now to FIG. 3, an exemplary embodiment is shown that demonstrates the growth of *P. aeruginosa* at 37° C. with 2.5 g/L exogenous rhamnolipids supplied as the sole carbon source and 2.5 g/L ammonium chloride supplied as the nitrogen source. At 19 hours after inoculation, the cells/ml in the culture reached levels comparable to those achieved when culturing for 18-24 hours in complex media ($1 \times 10^9$-$1 \times 10^{10}$ cells/ml).

Figure 4:
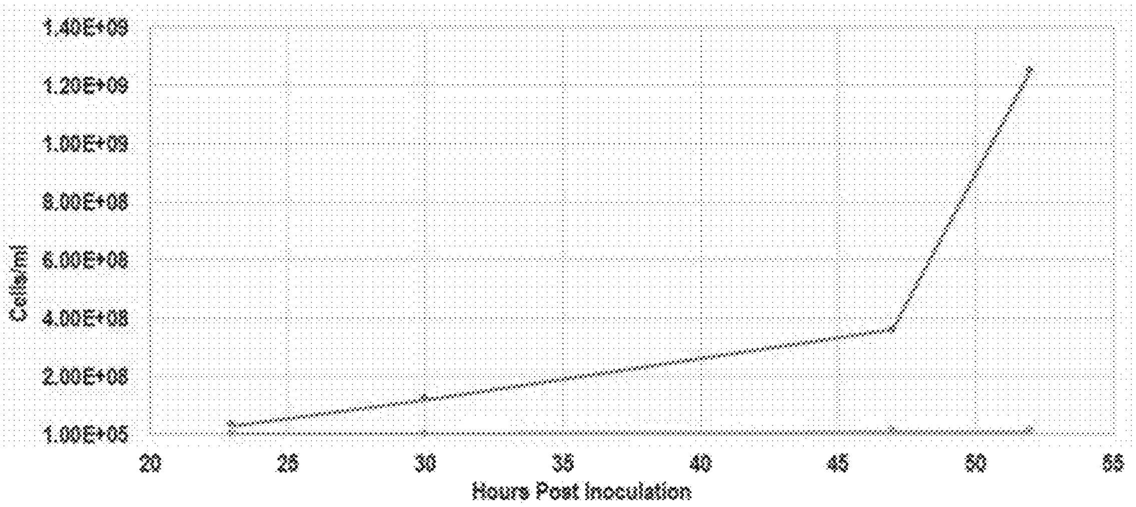
FIG. 4 is a graph showing growth of *P. aeruginosa* with hexadecane as the sole carbon source.

Referring now to FIG. 4, an exemplary embodiment is shown that demonstrates growth of *P. aeruginosa* at 37° C. when 1% w/v hexadecane is incorporated in mg/L amounts to a minimal salt media as the sole carbon source. The 1% w/v hexadecane was supplied as sole carbon source with either 1.9 (blue) or 3.8 g/L ammonium nitrate (orange) as the nitrogen source. Slightly over 50 hours after inoculation, the cells/ml in the culture including 1.9 g/L ammonium nitrate reach levels comparable to those achieved when culturing for 18-24 hours in complex media ($1 \times 10^9$-$1 \times 10^{10}$ cells/ml), while supplying 3.8 g/L of ammonium nitrate had an inhibitory effect of the growth of the strain. FIGS. 2 and 4 demonstrate that the type, and amount, of nitrogen source used impacts growth curves and can determine whether a given cell culture can reach levels of cell density comparable to those achieved in common laboratory medium. Without wishing to be bound by theory, these effects are also dependent on other fermentation variables such as the amount of type of carbon sources and the *Pseudomonas* sp. strain.

Figure 5:
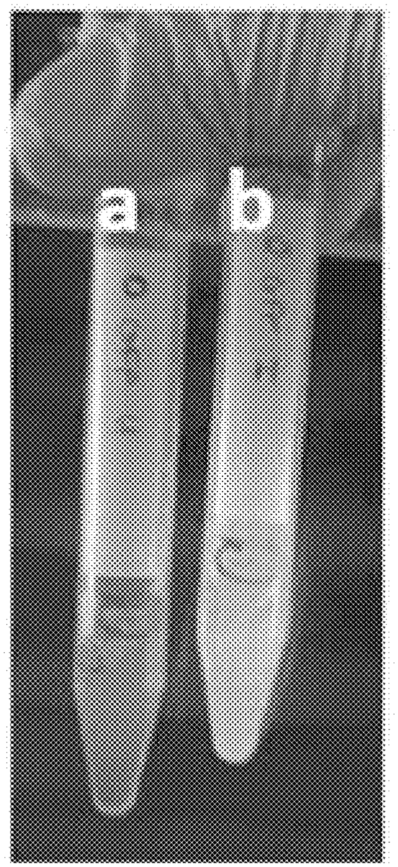
FIG. 5 is an image showing lysate from a culture of *Pseudomonas* sp. bacteria with exogenous genes encoding green fluorescent protein (GFP) with and without isopropyl ß-D-1-thiogalactopyranoside (IPTG)

Referring now to FIG. 5, the production of recombinant green fluorescent protein (GFP) expression in *P. oleovorans* was demonstrated using conventional Luria broth for the cell culture. The small molecule isopropyl ß-D-1-thiogalactopyranoside (IPTG) was used to induce recombinant protein production. (A) shows lysate of culture grown without IPTG added under UV light, while (B) shows lysate of culture grown in the presence of IPTG to induce GFP production under UV light.

Figure 6A:
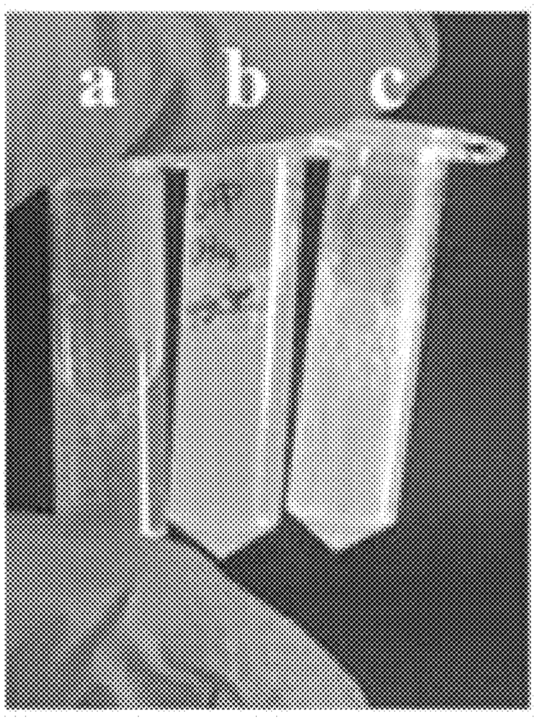
FIG. 6A is an image showing lysate from a culture of *P. oleovorans* bacteria with exogenous genes encoding GFP during expression of the GFP using hexadecane as the sole carbon source in the cell culture.
Figure 6B:
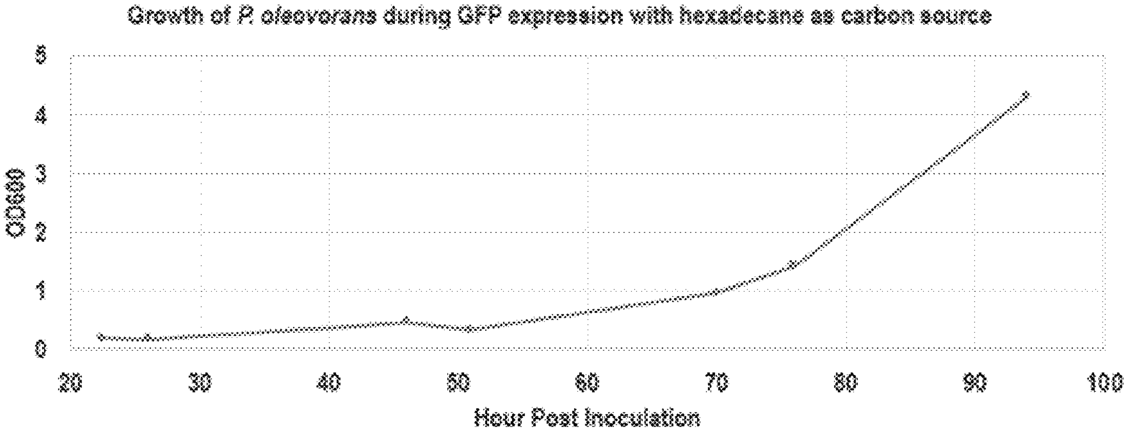
FIG. 6B is a graph showing growth of *P. oleovorans* bacteria with exogenous genes encoding GFP during expression of the GFP using hexadecane as the sole carbon source in the cell culture.

Referring now to FIGS. 6A and 6B, an exemplary embodiment is shown that demonstrates GFP production from *P. oleovorans* when using hexadecane as the carbon source in the cell culture. Referring specifically to FIG. 6A, differences in fluorescence under ultra-violet light between a culture induced for GFP production and an uninduced culture demonstrate the production of the recombinant protein. Referring specifically to FIG. 6B, growth in the minimal media was achieved by supplying 1% w/v of hexadecane as the carbon source and 2.5 g/L of ammonium chloride as the nitrogen source. In some embodiments, the protein product is produced by engineered *Pseudomonas* bacteria while growing in media containing a mixture of natural and synthetic carbon sources.

Figure 7:
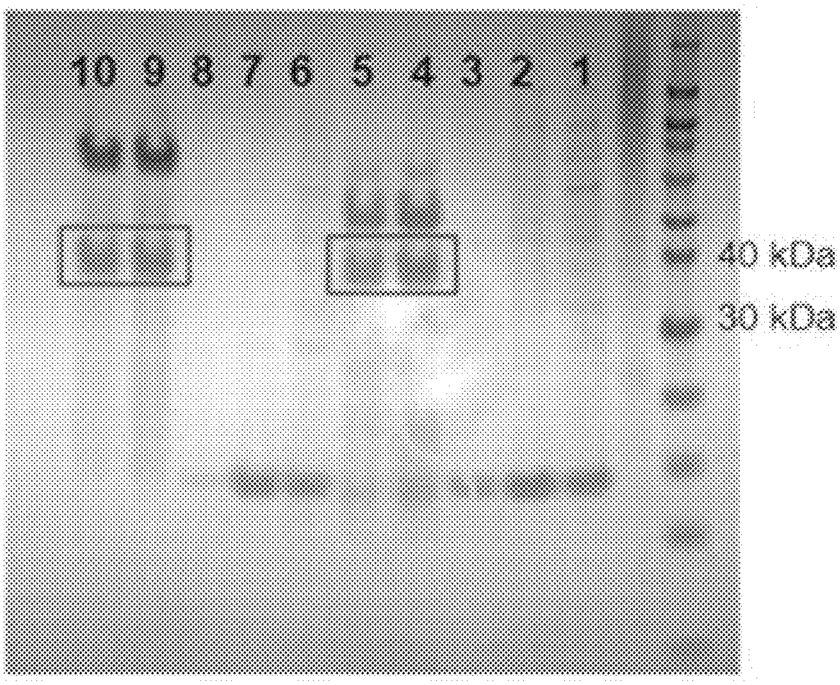
FIG. 7 is an image confirming production of recombinant silk protein produced in *P. aeruginosa*, purified with chromatography.
Figure 8:
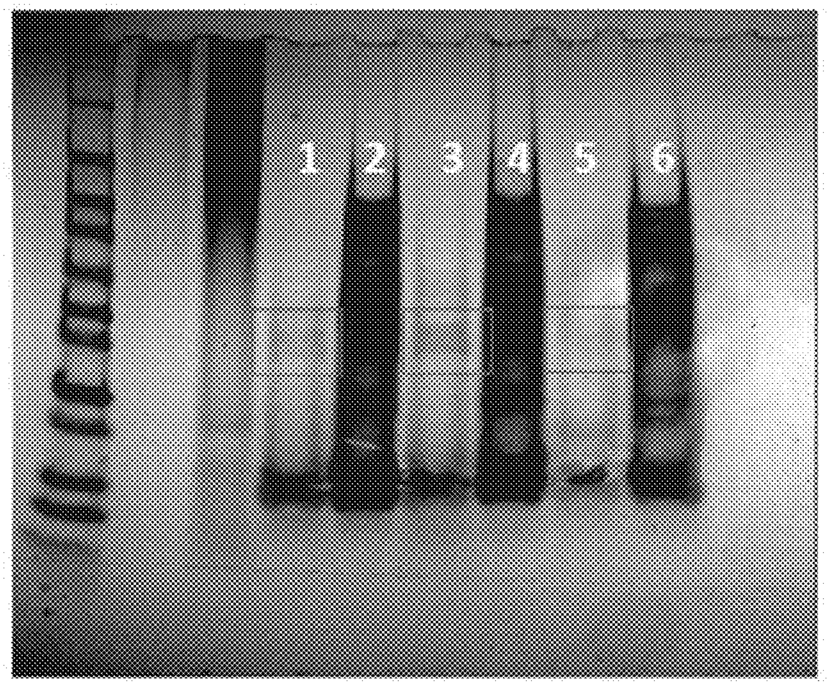
FIG. 8 is an image confirming production of recombinant silk protein produced in *P. aeruginosa*, purified with heat treatments.

Referring now to FIGS. 7 and 8, an exemplary embodiments are shown that demonstrate the production of recombinant silk protein in *P. aeruginosa* using conventional Luria broth for the cell culture. FIG. 7 specifically verifies the production of histidine-tagged recombinant silk proteins using nickel-affinity chromatography. FIG. 8 specifically shows purification of recombinant silk proteins through the thermal treatment of the raw lysate of the cell culture at 80° C.

Figure 9:
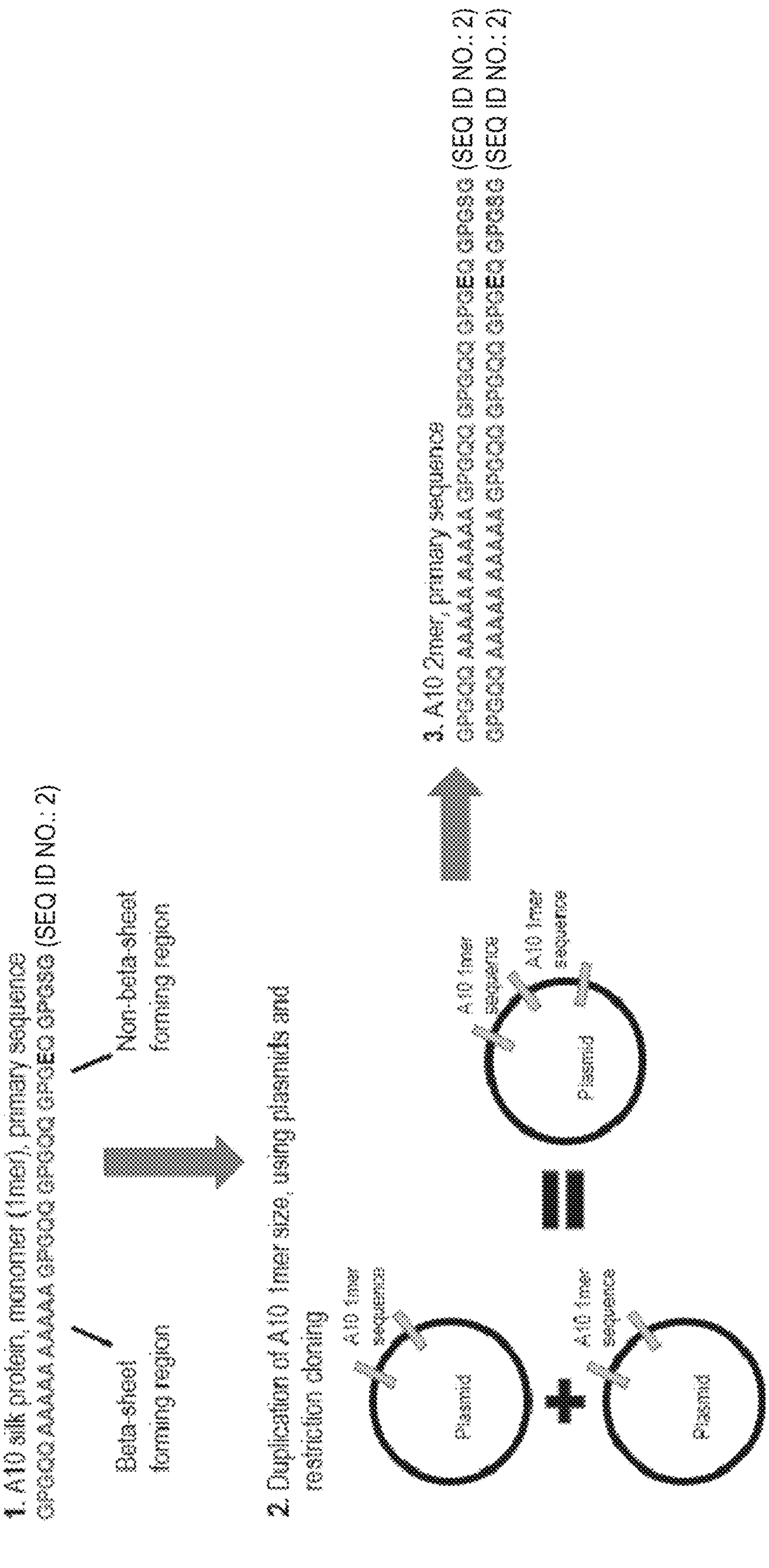
FIG. 9 is a flowchart portraying the design of recombinant silk proteins according to some embodiments of the present disclosure.

Referring now to FIG. 9, some embodiments of the present disclosure are directed to a recombinant bacterium. In some embodiments, the recombinant bacterium is configured for use in embodiments of the methods for the production of one or more desired products using hydrocarbyl materials as a carbon source described in the present disclosure.

As discussed above, in some embodiments, the recombinant bacterium is a *Pseudomonas* sp. bacterium including one or more biosynthetic pathways that utilize a target carbon source as a source of nutrients. In some embodiments, the *Pseudomonas* sp. bacterium utilizes nutrient sources derived from post-consumer petroleum-based plastic waste. In some embodiments, the *Pseudomonas* sp. bacterium expresses one or more PETases for degrading plastic into a usable carbon source. In some embodiments, the target carbon source includes exogenous rhamnolipids; hydrocarbyl groups including between about 5 and about 32 carbon atoms; pyrolysis products of a polyolefin; pyrolysis products of a polyester; a polyethylene component including polyethylene terephthalate, pyrolysis products of a polyethylene, or combinations thereof; or combinations thereof. In some embodiments, the *Pseudomonas* sp. bacteria includes *P. aeruginosa* RR1, *P. aeruginosa* NCIMB 14923, *P. oleovorans, P. putida* GPo1, or combinations thereof.

In some embodiments, the recombinant *Pseudomonas* sp. bacterium includes one or more genes encoding the desired products. In some embodiments, the recombinant *Pseudomonas* sp. bacterium includes one or more copies of the genes. In some embodiments, the one or more genes are exogenous to the recombinant *Pseudomonas* sp. bacterium. In some embodiments, the one or more genes encode silk proteins, fluorescent proteins, elastin-like proteins, or combinations thereof. In some embodiments, the one or more genes are composed of a plurality of gene fragments. In some embodiments, at least one of these gene fragments is multiplied so that the recombinant *Pseudomonas* sp. bacterium includes and expresses multiple copies of the gene fragment as a part of the expression of the overall inserted gene. In some embodiments, at least one of the gene fragments is multiplied between about 2 times and about 64 times.

In some embodiments, the silk proteins are natural silk proteins, recombinant silk proteins, or combinations thereof. Generally, silk fibroin proteins include non-repetitive N and C-terminus domains and a highly repetitive core domain. The primary sequence of silk fibroin drives the structure, properties, and functionality of silk. For example, silk fibroin derived from the *Bombyx mori* silkworm has a 391 kDa heavy chain linked to a 26 kDa light chain by a disulfide bond. The heavy chain, which dominates the mechanical properties of *B. mori* silk, has a repetitive core domain with 12 rigid segments bearing long stretches of glycine-X (GX) repeats, where X is most commonly alanine (A), serine(S), or tyrosine (Y). These GX repeats favor antiparallel beta-sheet secondary structure, which have a further tendency for assembly into crystalline domains detectable by characteristic Bragg peaks in X-ray diffraction. In particular, GAAS, GAGAGS, and GAGAGY are commonly encountered motifs in these rigid segments. The flexible linker segments between the rigid segments are nearly identical in sequence and include a non-repetitive 25 amino acid sequence that, notably, includes the proline (P), which generally disrupts secondary structure, and glutamic acid (E), which is negatively charged at physiological pH.

The primary sequence of spider silk fibroin (also known as spidroin) resembles *B. mori* silk fibroin in that the repetitive core domain contains segments of beta-sheet forming amino acid alternate with segments of amino acids that do not tend to form beta-sheets. Dragline silks are composed of two different spidroins, such as major ampullate I (MaSp1) and major ampullate 2 (MaSp2) spidroins produced by *Nephila clavipes*. One "diblock" of a beta-sheet/non-beta-sheet segment is typically 10-50 residues long, and this diblock may repeat several hundred times in the core domain. The beta-sheet-forming segments of dragline spidroins often include about 6-9 tandem alanine residues. The non-beta-sheet-forming segments of dragline spidroins often include multiple repeats of GPGXX and GGX motifs, where X is commonly tyrosine (Y), glutamine (Q), or leucine (L). The recombinant proteins encoded in several embodiments of the present disclosure resemble dragline silk fibroin, though it should be noted that spiders can produce several other types of silk aside from dragline silk.

Some embodiments of the present disclosure invention include a library of genes and proteins that mimic natural silk fibroin, the genes being inserted into the *Pseudomonas* sp. bacteria of the present disclosure to generate the expressed proteins as a product. In some embodiments, these proteins are based on a plurality of distinct and purposefully designed gene fragments or "monomer units," which are comprised of a diblock of beta-sheet-forming and non-beta-sheet-forming amino acid sequences. As discussed above, in some embodiments, these monomer units are multiplied in size from a single monomer to tandem repeats of 2, 4, 8, 16, 32, and 64 units to form larger proteins. FIG. 9 demonstrates the design of a representative monomer unit for a protein that mimics natural fibroin, "A10," which has beta-sheet-forming polyalanine regions and glycine-rich non-beta-sheet-forming regions. A plasmid-based procedure is used to duplicate the size of the A10 gene to create larger genes that code for polymeric proteins that include tandem repeats of the A10 monomer sequence. Using this procedure, an A10 2 mer gene can be formed by combining two A10 1 mer sequences. The process can be repeated using two A10 2 mer genes to form an A10 4 mer gene.

In some embodiments, the genes encoding silk proteins include one or more gene fragments coding for GPGQQ AAAAA GPGQQ GPGQQ GPGQQ GPGEQ GPGSG (SEQ ID NO.: 1), GPGQQ AAAAA AAAAA GPGQQ GPGQQ GPGEQ GPGSG (SEQ ID NO.: 2), or combinations thereof. In some embodiments, the proteins produced by expressing the one or more genes include the primary monomer sequence GPGQQ AAAAA GPGQQ GPGQQ GPGQQ GPGEQ GPGSG (SEQ ID NO.: 1) repeated one or more times. In some embodiments, the proteins produced by expressing the one or more genes include the primary monomer sequence GPGQQ AAAAA AAAAA GPGQQ GPGQQ GPGEQ GPGSG (SEQ ID NO.: 2), repeated one or more times. In some embodiments, the proteins produced by the embodiments of the present disclosure include functional equivalents of the sequences described above, e.g., peptides with greater than about 85% sequence identity with the above-identified peptides that substantially retain the function of those proteins.

In some embodiments, the genes encoding elastin-like proteins include one or more gene fragments coding for V-P-G-X-G repeats, wherein X is any amino acid other than proline. In some embodiments, the genes encoding elastin-like proteins include one or more gene fragments coding for VPGAGVPGAGVPGAGVPGAGVPGYGVPGAGVPGAGVPGAGVPGAGVPGYG (SEQ ID NO: 3). In some embodiments, the gene fragments coding for elastin-like proteins also include a sequence encoding for GRGDS, e.g., VPGAGVPGAGVPGAGVPGAGVPGYGVPGAGVPGAGVPGAGVPGAGVPGYGVPGAGV PGAGVPGAGVPGAGVPGYGVPGAGVPGAGVPGAGVPGAGVPGYGG-RGDS (SEQ ID NO: 4).

Figure 10:
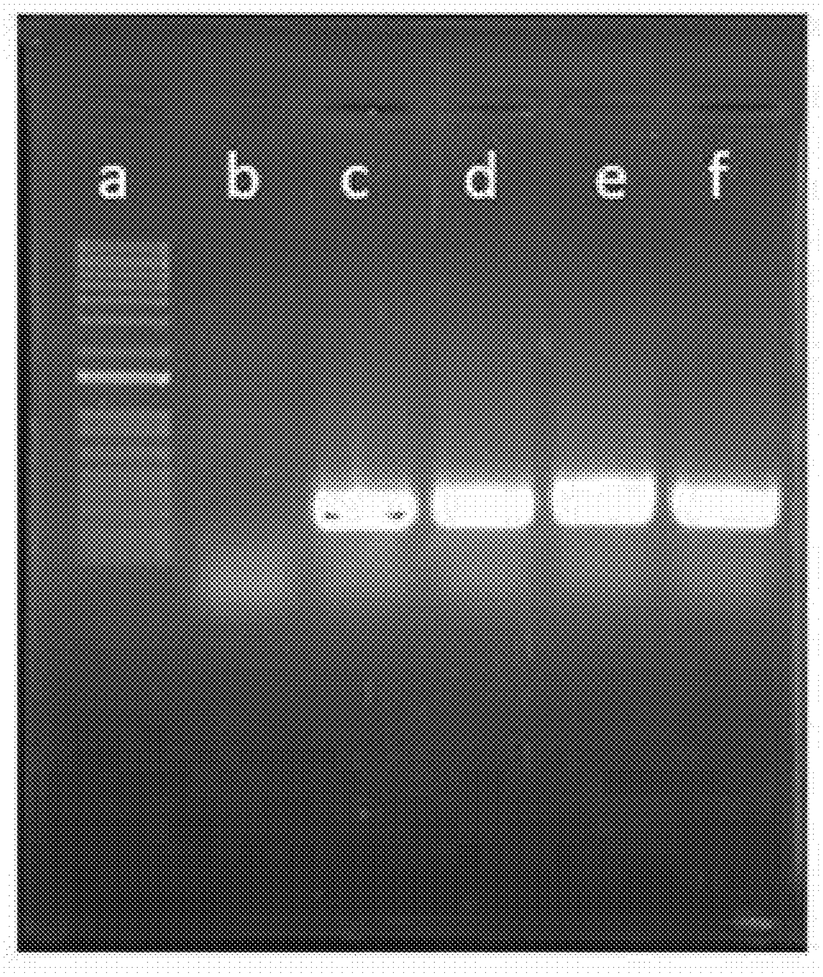
FIG. 10 is an image verifying the insertion of recombinant silk genes at the attTN7 site of a *P. aeruginosa* genome via pUC18-derived suicide vectors according to some embodiments of the present disclosure.

In some embodiments, the one or more genes are inserted into the genome of the *Pseudomonas* sp. bacterium. In some embodiments, the one or more genes are inserted at the attTn7 site of the recombinant *Pseudomonas* sp. bacterium under the control of a tac promoter and a lac operon. In some embodiments, the genomically integrated recombinant genes are integrated using suicide vectors, e.g., pUC18-derived suicide vectors. Referring now to FIG. 10, a PCR reaction was used to confirm the insertion of a recombinant silk genes at the attTN7 site of the *P. aeruginosa* genome via pUC18-derived suicide vectors in an exemplary embodiment of the present disclosure. A 300 base pair DNA fragment can be PCR amplified and visualized through gel electrophoresis from colonies which have successfully had the recombinant gene integrated, while colonies of the wild-type variety show no amplified DNA bands in gel electrophoresis.

In some embodiments, the one or more genes are included in the bacterium in a recombinant plasmid. In some embodiments, the recombinant plasmid is compatible with the particular *Pseudomonas* sp. bacteria being used. The plasmid is deemed suitable by the presence of promoters which are compatible with *Pseudomonas* sp. transcriptional capabilities, by its ability to replicate in *Pseudomonas* sp., by not deleteriously competing with endogenous plasmid replication pathways of *Pseudomonas* sp., by not fatally disrupting plasmid segregation during replication, etc., or combinations thereof. In some embodiments, the plasmid includes a pSEVA plasmid backbone, e.g., pBb(RK2)1k-X recombinant plasmid, pSEVA221, etc., or other vectors derived from a pSEVA backbone. In some embodiments, the recombinant plasmid includes inducible expression of the one or more genes with IPTG.

Figure 11:
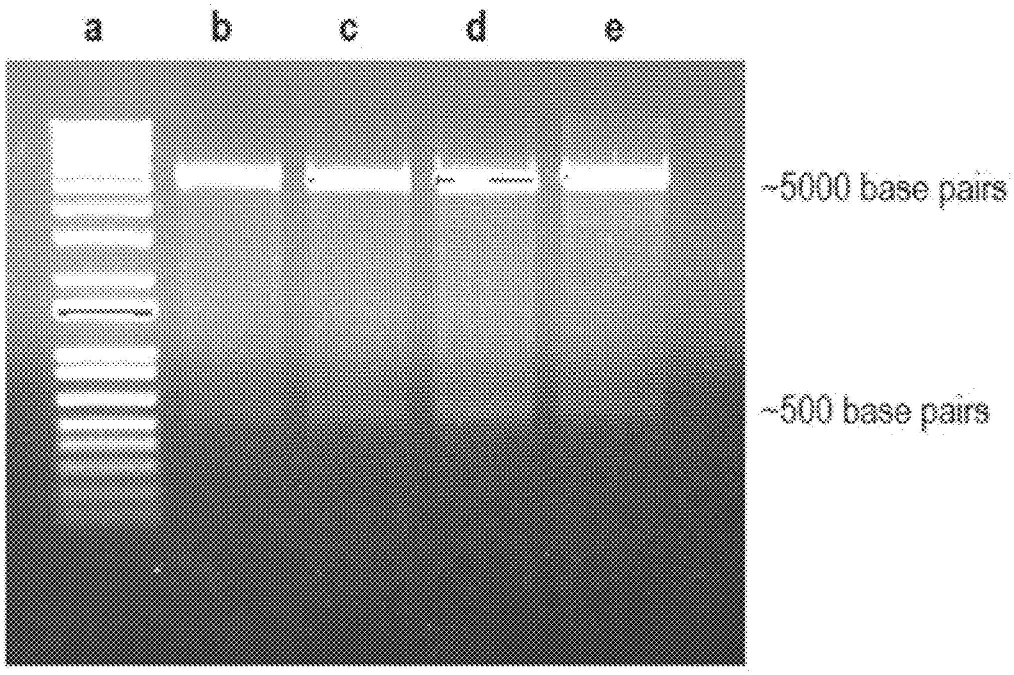
FIG. 11 is an image verifying the insertion of recombinant silk genes into *P. aeruginosa* according to some embodiments of the present disclosure.

Referring now to FIG. 11, gel electrophoresis was used to verify the insertion of recombinant silk genes into *P. aeruginosa* using a replicative plasmid. The GFPuv gene of plasmid vector pBb(RK2)1k-GFPuv was removed using restriction cloning and a 500 base pair silk gene was inserted into the vector backbone (5000 base pairs) to create pBb (RK2)1k-silk. The vector was inserted into the *Pseudomonas* sp. and its uptake and replication were confirmed via a plasmid extraction, restriction digest, and gel electrophoresis. Plasmid isolated from four different *Pseudomonas* sp. cultures show the correct size for the vector backbone and silk gene when digested with restriction enzymes. The RK2 replicon and trc promoter present on the vector facilitate its maintenance and the expression of the recombinant silk gene in *Pseudomonas* sp.

In some embodiments, the recombinant *Pseudomonas* sp. are cultured in suitable growth conditions, as discuss above with respect to method 100. In some embodiments, the recombinant *Pseudomonas* sp. are cultured with one or more of the carbon sources described above. In some embodiments, the carbon sources are fed to the recombinant *Pseudomonas* sp. in a batch process, semi-batch process, continuous process, or combinations thereof.

Figure 12:
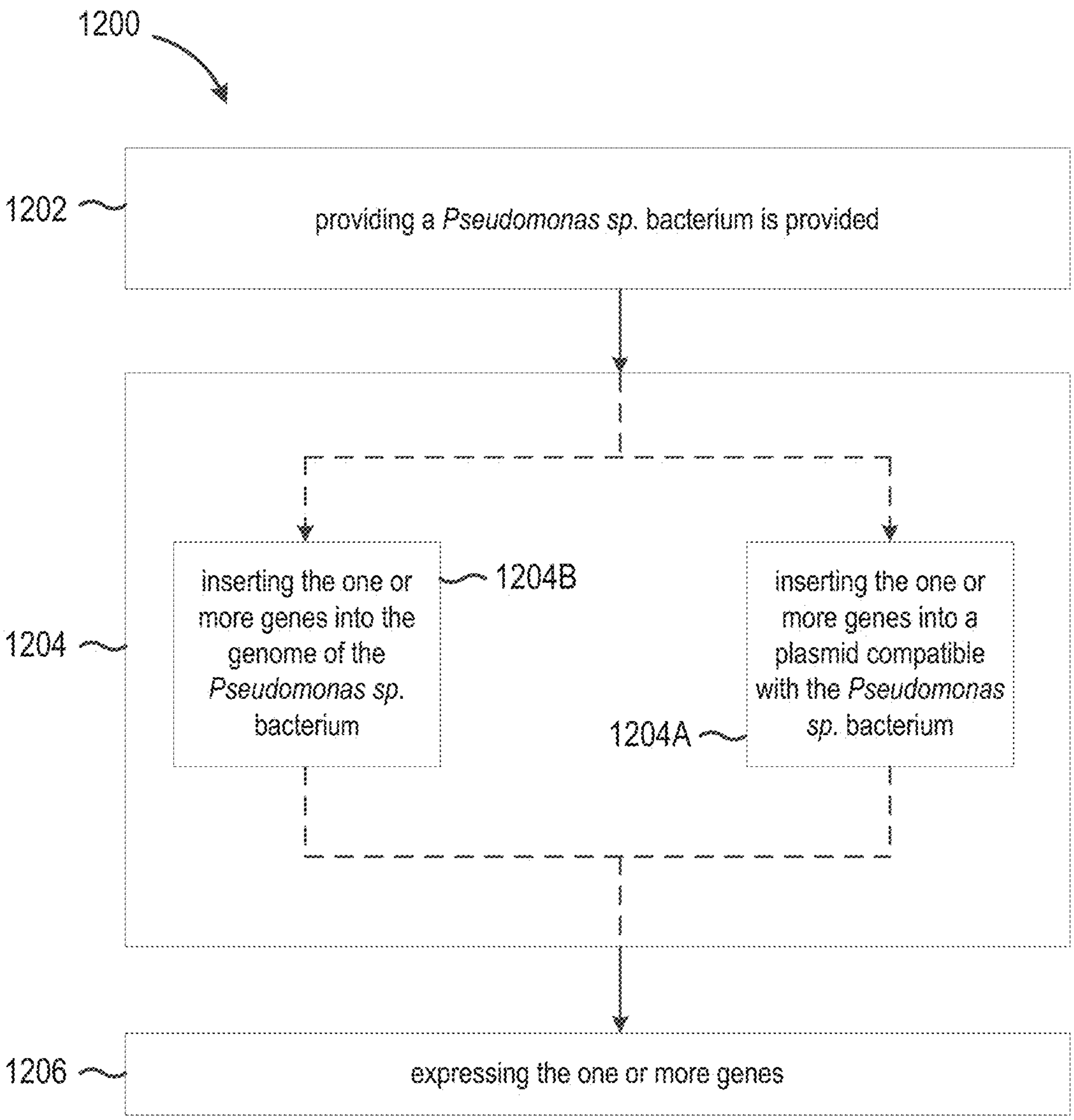
FIG. 12 is a chart of a method for producing a desired product using recombinant bacteria according to some embodiments of the present disclosure.

Referring now to FIG. 12, some embodiments of the present disclosure are directed to a method 1200 for producing a recombinant desired product. At 1202, a *Pseudomonas* sp. bacterium is provided. As discussed above, in some embodiments, the *Pseudomonas* sp. bacterium includes one or more biosynthetic pathways that utilize a hydrocarbyl material as a carbon source. In some embodiments, the *Pseudomonas* sp. bacterium utilizes nutrient sources derived from post-consumer petroleum-based plastic waste. In some embodiments, the hydrocarbyl material includes exogenous rhamnolipids; hydrocarbyl groups including between about 5 and about 32 carbon atoms; pyrolysis products of a polyolefin; pyrolysis products of a polyester; a polyethylene component including polyethylene terephthalate, pyrolysis products of a polyethylene, or combinations thereof; or combinations thereof. In some embodiments, the *Pseudomonas* sp. bacterium includes *P. aeruginosa* RR1, *P. aeruginosa* NCIMB 14923, *P. oleovorans, P. putida* GPo1, or combinations thereof.

At 1204, one or more genes encoding the desired product are inserted into the *Pseudomonas* sp. bacterium to form a recombinant *Pseudomonas* sp. bacterium. In some embodiments, the one or more genes are composed of a plurality of gene fragments. In some embodiments, at least one of these gene fragments is multiplied so that the recombinant *Pseudomonas* sp. bacterium includes multiple copies of the gene fragment. In some embodiments, at least one of the gene fragments is multiplied between about 2 times and about 64 times.

In some embodiments, at 1204A, the one or more genes are inserted into the genome of the *Pseudomonas* sp. bacterium. In some embodiments, the one or more genes are inserted at the attTn7 site of the recombinant *Pseudomonas* sp. bacterium under the control of a tac promoter and a lac operon. In some embodiments, one or more gene fragments are inserted into the genome and multiplied within the genome itself. In some embodiments, one or more gene fragments are multiplied to produce the gene prior to insertion into the genome of the *Pseudomonas* sp. bacterium.

In some embodiments, at 1204B, the one or more genes are inserted into a plasmid compatible with the *Pseudomonas* sp. bacterium. In some embodiments, the plasmid includes a pSEVA plasmid backbone, e.g., pBb(RK2)1k-GFPuv, pSEVA221, etc. In some embodiments, a plasmid compatible with the *Pseudomonas* sp. bacterium is provided. In some embodiments, the one or more genes are inserted into the plasmid to form a recombinant plasmid. In some embodiments, a plurality of gene fragments encoding the desired product are inserted into the plasmid to form a recombinant plasmid. In some embodiments, the recombinant plasmid is transformed into the *Pseudomonas* sp. bacteria to form a recombinant *Pseudomonas* sp. bacterium.

As discussed above, in some embodiments, the one or more genes encode silk proteins, fluorescent proteins, elastin-like proteins, or combinations thereof. In some embodiments, the silk proteins are natural silk proteins, recombinant silk proteins, or combinations thereof. In some embodiments, the genes encoding silk proteins include one or more gene fragments coding for GPGQQ AAAAA GPGQQ GPGQQ GPGQQ GPGEQ GPGSG (SEQ ID NO.: 1), GPGQQ AAAAA AAAAA GPGQQ GPGQQ GPGEQ GPGSG (SEQ ID NO.: 2), or combinations thereof. In some embodiments, the genes encoding elastin-like proteins include one or more gene fragments coding for V-P-G-X-G repeats, wherein X is any amino acid other than proline. In some embodiments, the genes encoding elastin-like proteins include one or more gene fragments coding for VPGAGVP-GAGVPGAGVPGAGVPGYGVPGAGVPGAGVPGAG-VPGAGVPGYG (SEQ ID NO: 3). In some embodiments, the gene fragments coding for elastin-like proteins also include a sequence encoding for GRGDS, e.g., VPGAGVP-GAGVPGAGVPGAGVPGYGVPGAGVPGAGVPGAGV-PGAGVPGYGVPGAGV PGAGVPGAGVPGAGVPGYG-VPGAGVPGAGVPGAGVPGAGVPGYGGRGDS (SEQ ID NO: 4). In some embodiments, the fluorescent protein includes green fluorescent protein.

At 1206, the one or more genes are expressed. As discussed above, in some embodiments, upon expression, the recombinant *Pseudomonas* sp. bacterium produce one or more desired products that can be subsequently collected.

Methods and systems of the present disclosure are advantageous to produce recombinant silk products from waste feedstock. *Pseudomonas* sp. represent an advantageous chassis for recombinant silk production. The strains utilized in the methods of the present disclosure demonstrate ability to naturally use plastic waste as a carbon (food) source, as well as their high growth rates when grown in plastic waste products. The body of literature exploring the upcycling capabilities of bacteria has grown considerably in the past five years. For instance, platforms such as *E. coli* and *B. succiniciproducens* have been used to produce high-value metabolites from the upcycling of organic biomass such as starch and lignin waste. Likewise, the upcycling of inorganic waste (PET plastic) into higher-value compounds has been established in species such as *E. coli*. However, while current work examining bacterial upcycling has used both organic and inorganic waste (including plastic waste) as a feedstock, it has almost exclusively targeted endogenous bacterial biopolymers or secondary metabolites as products. Bacterial upcycling of waste into recombinant proteins is far rarer, and studies in this space use organic waste as a feedstock, such as cheese whey or waste algae. Moreover, none of these studies target recombinant silk or similar proteins as a product. Thus, the present disclosure advantageously demonstrated production of recombinant silk proteins through a bacterial upcycling process, as well as the production of recombinant proteins via the bacterial upcycling of plastic waste. Such high value recombinant proteins include recombinant silk fibroin or spidroin, which have diverse uses as biocompatible and biodegradable materials for biomedical applications, such as drug delivery, implants, and tissue engineering; consumer products, such as cosmetics, sustainable clothing, and textiles and textiles; and food packaging, such as coatings for food preservation.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A recombinant *Pseudomonas* sp. bacterium capable of utilizing the following carbon sources:
   - exogenous rhamnolipids;
   - hydrocarbyl groups including between 5 and 32 carbon atoms;
   - pyrolysis products of a polyolefin;
   - pyrolysis products of a polyester;
   - a polyethylene component including polyethylene terephthalate, pyrolysis products of a polyethylene, or combinations thereof;
   - or combinations thereof;

wherein the bacterium comprises one or more genes encoding silk proteins, wherein the one or more genes comprise gene fragments including a construct having between 2 and 64 repeated fragments, wherein the gene fragments encode the amino acid sequence of SEQ ID NO: 1 or SEQ ID NO:2.

2. The bacterium according to claim 1, wherein: the *Pseudomonas* sp. bacterium is selected from a group consisting of *P. aeruginosa* RR1, *P. aeruginosa* NCIMB 14923, *P. oleovorans, P. putida* GPol, and combinations thereof.

3. The bacterium according to claim 1, wherein the one or more genes encoding silk proteins are downstream of a tac promoter and lac operon and are inserted at an attTn7 site of the *Pseudomonas* bacterial chromosome.

4. The bacterium according to claim 1, wherein the one or more genes encoding silk proteins are within a recombinant plasmid, wherein the recombinant plasmid is a pSEVA plasmid comprising an isopropyl 13-D-1-thiogalactopyranoside-inducible promoter.

* * * * *